United States Patent
Kang et al.

(10) Patent No.: US 9,476,961 B2
(45) Date of Patent: Oct. 25, 2016

(54) METHOD AND APPARATUS FOR CORRECTING IMPEDANCE MEASURED BY SENSOR INCLUDED IN WEARABLE DEVICE

(71) Applicant: SAMSUNG ELECTRONICS CO., LTD., Suwon-si (KR)

(72) Inventors: Jaemin Kang, Seoul (KR); Sangyun Park, Hwaseong-si (KR); Hyoyoung Jeong, Seoul (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/665,766

(22) Filed: Mar. 23, 2015

(65) Prior Publication Data

US 2016/0054423 A1    Feb. 25, 2016

(30) Foreign Application Priority Data

Aug. 25, 2014 (KR) .................. 10-2014-0111043

(51) Int. Cl.

| | | |
|---|---|---|
| G06K 9/36 | (2006.01) | |
| G01R 35/00 | (2006.01) | |
| G06T 7/00 | (2006.01) | |
| G06F 1/16 | (2006.01) | |
| A61B 5/00 | (2006.01) | |
| A61B 5/053 | (2006.01) | |

(52) U.S. Cl.
CPC ............ *G01R 35/005* (2013.01); *A61B 5/0537* (2013.01); *A61B 5/4872* (2013.01); *G06F 1/163* (2013.01); *G06T 7/0042* (2013.01); *G06T 2207/10004* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 6,694,182 | B1 * | 2/2004 | Yamazaki .......... A61B 5/02438 |
| | | | 600/547 |
| 2013/0234927 | A1 | 9/2013 | Roh |
| 2016/0012749 | A1 * | 1/2016 | Connor .................. G09B 5/00 |
| | | | 600/13 |

FOREIGN PATENT DOCUMENTS

| | | |
|---|---|---|
| JP | 3140916 U | 4/2008 |
| JP | 2013-123448 A | 6/2013 |
| JP | 2013-183975 A | 9/2013 |
| JP | 5511503 B2 | 6/2014 |

* cited by examiner

*Primary Examiner* — Brian P Werner
(74) *Attorney, Agent, or Firm* — Sughrue Mion, PLLC

(57) ABSTRACT

Methods and apparatuses for correcting an impedance measured by a sensor included in a wearable device are provided. In an exemplary embodiment, the methods includes: measuring, from an image including the wearable device and arms of a user, a first angle between a straight line connecting a left elbow joint of the user and a camera device for photographing the image and a straight line connecting the left elbow joint and the wearable device, a second angle between a straight line connecting the left elbow joint and the wearable device and a straight line connecting the wearable device and a right elbow joint of the user, a third angle between a straight line connecting the right elbow joint and the wearable device and a straight line connecting the right elbow joint and the camera device, and a fourth angle between a straight line connecting the right elbow joint and the camera device and a straight line connecting the left elbow joint and the camera device.

20 Claims, 6 Drawing Sheets

400

| ANGLE STRAIGHT LINES RESPECTIVELY CONNECTING ELBOW JOINTS AND WEARABLE DEVICE (200) | ANGLE BETWEEN STRAIGHT LINE CONNECTING LEFT ELBOW JOINT AND WEARABLE DEVICE AND STRAIGHT LINE CONNECTING LEFT ELBOW JOINT AND PHOTOGRAPHING UNIT (210) | ANGLE BETWEEN STRAIGHT LINE CONNECTING RIGHT ELBOW JOINT AND WEARABLE DEVICE 110 AND STRAIGHT LINE CONNECTING RIGHT ELBOW JOINT AND PHOTOGRAPHING UNIT (220) | ANGLE BETWEEN STRAIGHT LINES RESPECTIVELY CONNECTING PHOTOGRAPHING UNIT AND BOTH ELBOW JOINTS (230) | IMPEDANCE VARIATION RATE (410) |
|---|---|---|---|---|
| 100° | 80° | 60° | 120° | 0.8 |
| 80° | 100° | 80° | 100° | 0.6 |
| 60° | 120° | 100° | 80° | 0.4 |

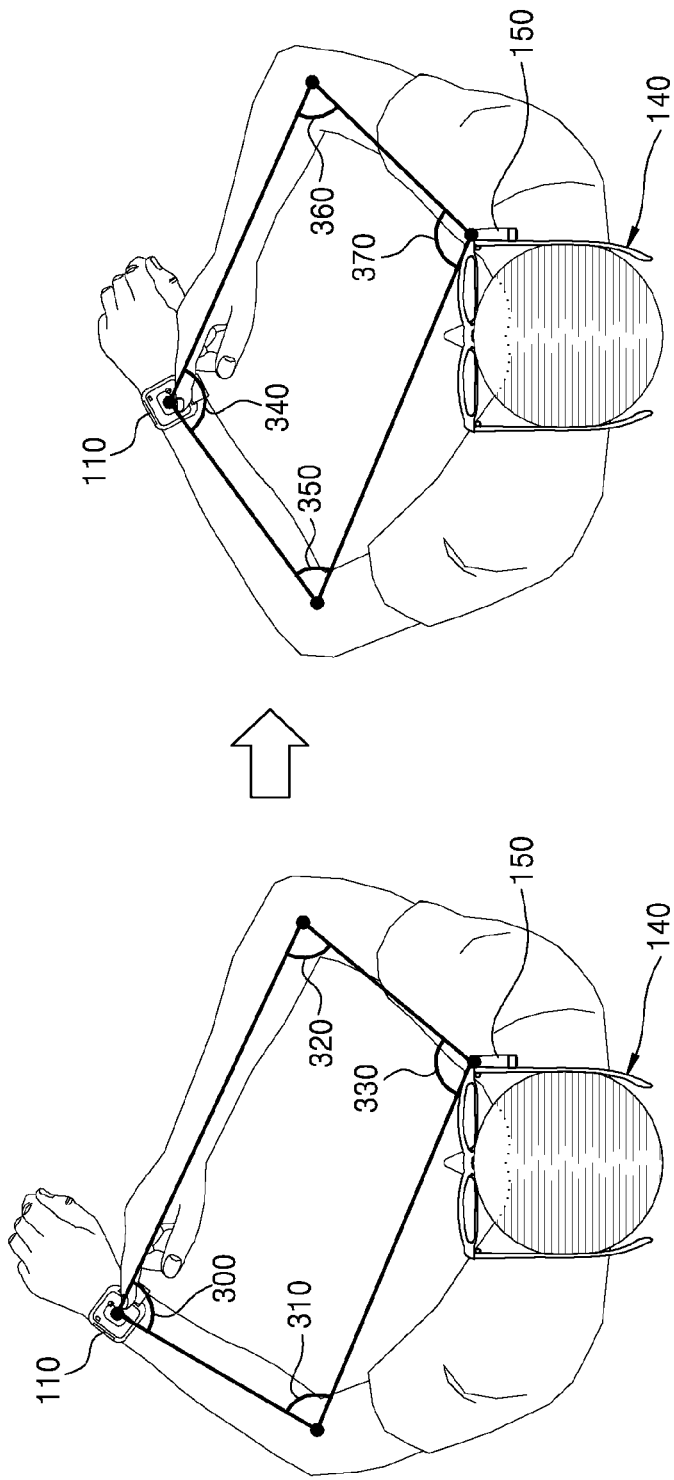

FIG. 4

| ANGLE STRAIGHT LINES RESPECTIVELY CONNECTING ELBOW JOINTS AND WEARABLE DEVICE (200) | ANGLE BETWEEN STRAIGHT LINE CONNECTING LEFT ELBOW JOINT AND WEARABLE DEVICE AND STRAIGHT LINE CONNECTING LEFT ELBOW JOINT AND PHOTOGRAPHING UNIT (210) | ANGLE BETWEEN STRAIGHT LINE CONNECTING RIGHT ELBOW JOINT AND WEARABLE DEVICE 110 AND STRAIGHT LINE CONNECTING RIGHT ELBOW JOINT AND PHOTOGRAPHING UNIT (220) | ANGLE BETWEEN STRAIGHT LINES RESPECTIVELY CONNECTING PHOTOGRAPHING UNIT AND BOTH ELBOW JOINTS (230) | IMPEDANCE VARIATION RATE (410) |
|---|---|---|---|---|
| 100° | 80° | 60° | 120° | 0.8 |
| 80° | 100° | 80° | 100° | 0.6 |
| 60° | 120° | 100° | 80° | 0.4 |

400

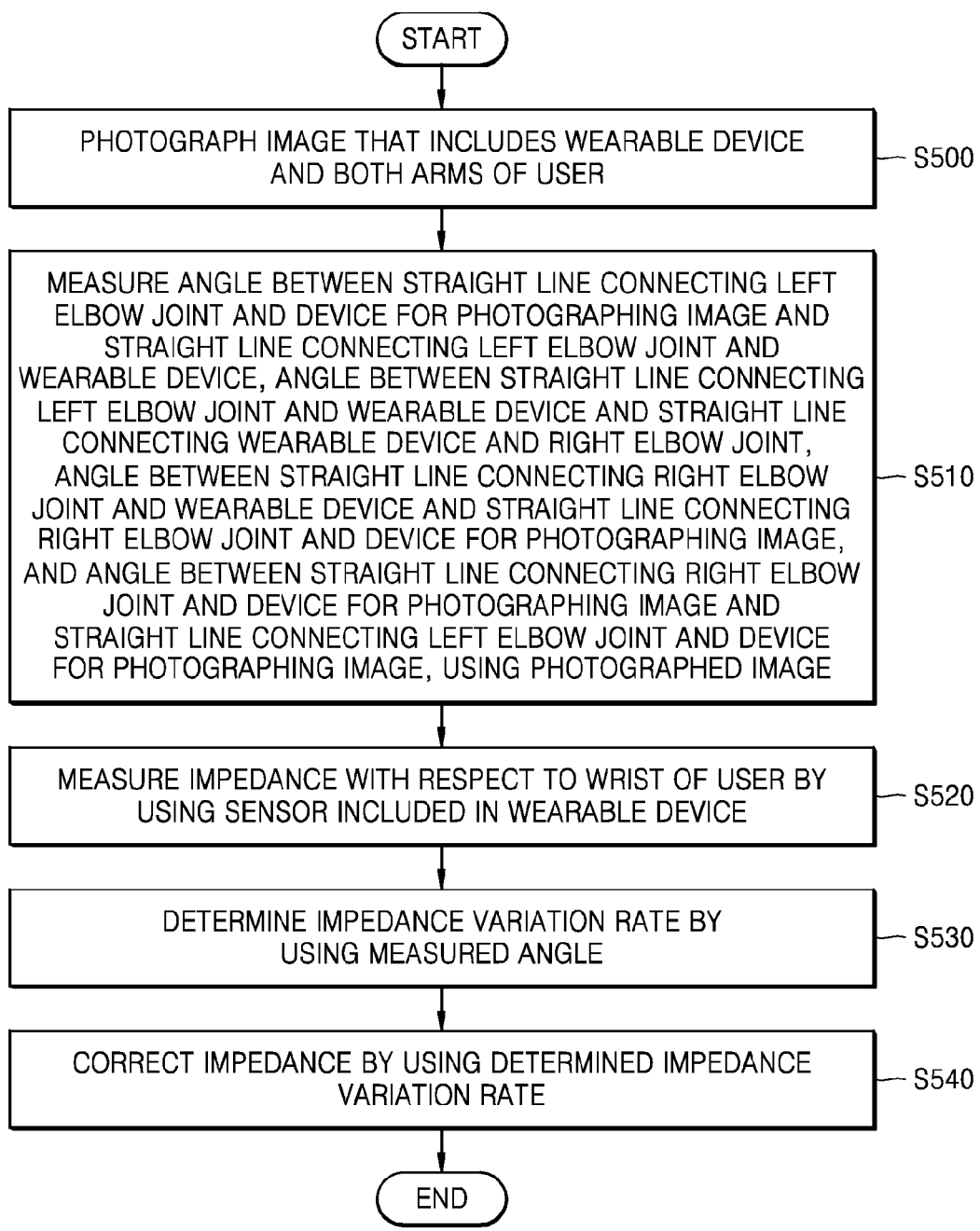

METHOD AND APPARATUS FOR CORRECTING IMPEDANCE MEASURED BY SENSOR INCLUDED IN WEARABLE DEVICE

CROSS REFERENCE TO RELATED APPLICATION

This application claims priority from Korean Patent Application No. 10-2014-0111043, filed on Aug. 25, 2014 in the Korean Intellectual Property Office, the disclosure of which is incorporated herein in its entirety by reference.

BACKGROUND

1. Field

Apparatuses and methods consistent with exemplary embodiments relate to methods and apparatuses for correcting an impedance measured by a sensor included in a wearable device.

2. Description of Related Art

Due to technological advances, many electronic devices are manufactured to have small and light structures. For example, wearable devices such as smart watches and smart glasses have been developed. A smart watch generally refers to a wrist watch that has advanced functions compared to a traditional watch. Smart glasses generally refer to a wearable computer mounted with a head-mounted display (HMD).

As an example, a wearable device may be classified into an independent device or a companion device. An independent device may include an input/output unit, an arithmetic Logic Unit (ALU), a storage unit, and a communication unit, and may be employed independently. A companion device refers to a device that may be used when a connection is established to a separate device such as a smartphone.

Since a wearable device is worn by a user on his/her body, the wearable device may also obtain a biometric signal from the user's body. Accordingly, wearable devices including various sensors have been developed.

SUMMARY

Exemplary embodiments provide methods and apparatuses for correcting an impedance measured by a sensor included in a wearable device, and a non-transitory computer-readable recording storage medium having stored thereon a computer program, which when executed by a computer, performs the methods.

According to an aspect of an exemplary embodiment, there is provided a method of correcting an impedance measured by a sensor included in a wearable device, the method including: measuring, from an image including the wearable device and arms of a user, by the wearable device, a first angle between a straight line connecting a left elbow joint of the user and a camera device for photographing the image and a straight line connecting the left elbow joint and the wearable device, a second angle between a straight line connecting the left elbow joint and the wearable device and a straight line connecting the wearable device and a right elbow joint of the user, a third angle between a straight line connecting the right elbow joint and the wearable device and a straight line connecting the right elbow joint and the camera device, and a fourth angle between a straight line connecting the right elbow joint and the camera device and a straight line connecting the left elbow joint and the camera device; measuring, by the sensor, the impedance of the user in response to the sensor being in contact with the user; determining, by the wearable device, a variation rate of the impedance by based on the first, second, third, and fourth angles; and correcting, by the wearable device, the impedance based on the determined variation rate of the impedance.

The determining may include determining the variation rate of the impedance based on a predetermined variation rate of the impedance which corresponds to the first, second, third, and fourth angles.

The determining may further include: photographing a moving picture including the wearable device and the arms of the user, while one hand of the user is in contact with the wearable device and the arms are moving; consecutively measuring impedance of the user by using the sensor, while photographing the moving picture; measuring a fifth angle between a straight line connecting the left elbow joint of the user and the camera device and a straight line connecting the left elbow joint and the wearable device, a sixth angle between a straight line connecting the left elbow joint and the wearable device and a straight line connecting the wearable device and the right elbow joint of the user, a seventh angle between a straight line connecting the right elbow joint and the wearable device and a straight line connecting the right elbow joint and the camera device, and an eighth angle between a straight line connecting the right elbow joint and the device for photographing the image and a straight line connecting the left elbow joint and the camera device based on the moving picture; and setting a variation rate of the impedance in correspondence with the fifth, sixth, seventh, and eight angles, by using the impedance which corresponds to the first, second, third, and fourth angles.

The consecutively measuring the impedance may include repeatedly measuring the impedance at a predetermined time period.

The determining may include determining the variation rate of the impedance based on a predetermined relation between at least one of the first, second, third, and fourth angles and the variation rate of the impedance.

The correcting may include measuring a body fat of the user based on the corrected impedance.

The wearable device may be a smart watch, and the image may be photographed by the camera device equipped with smart glasses.

The method may further include photographing the image while the smart watch is in contact with one hand of the user.

The method may further include photographing the image based on an input signal from the user.

The method may further include adjusting the variation rate based on quality of a contact between the sensor and the user.

According to an aspect of another exemplary embodiment, there is provided an apparatus including: an processor for measuring a first angle between a straight line connecting a left elbow joint of the user and a camera device for photographing the image and a straight line connecting the left elbow joint and the wearable device, a second angle between a straight line connecting the left elbow joint and the wearable device and a straight line connecting the wearable device and a right elbow joint of the user, a third angle between a straight line connecting the right elbow joint and the wearable device and a straight line connecting the right elbow joint and the camera device, and a fourth angle between a straight line connecting the right elbow joint and the camera device and a straight line connecting the left elbow joint and the camera device; a sensor configured to measure an impedance of the user in response to the sensor being in contact with the user; and a controller configured to determine a variation rate of the impedance based on at least one of the first, second, third, and fourth angles, and correct the impedance based on the determined variation rate of the impedance.

The apparatus may further include the camera device configured to photograph the image including the wearable device and the arms of the user.

The controller may determine the variation rate of the impedance based on a predetermined variation rate of the impedance which respectively corresponds to the first, second, third, and fourth angles.

The camera device may photograph a moving picture including the wearable device and the arms of the user while one hand of the user is in contact with the wearable device and the arms of the user are moving, the sensor may consecutively measure impedance of the user, while the moving picture is being photographed, the processor may measure a fifth angle between a straight line connecting a left elbow joint of the user and the camera device and a straight line connecting the left elbow joint and the wearable device, a sixth angle between a straight line connecting the left elbow joint and the wearable device and a straight line connecting the wearable device and a right elbow joint of the user, a seventh angle between a straight line connecting the right elbow joint and the wearable device and a straight line connecting the right elbow joint and the camera device, and an eighth angle between a straight line connecting the right elbow joint and the camera device and a straight line connecting the left elbow joint and the camera device based on the moving picture, and the controller may set a variation rate of the impedance in correspondence with the fifth, sixth, seventh, and eighth measured angles based on the impedance corresponding to the first, second, third, and fourth angles.

The sensor may repeatedly measure the impedances at a predetermined time period.

The controller may determine a variation rate of the impedance based on a predetermined relation between at least one of the first, second, third, and fourth angles and the variation rate of the impedance.

The controller may measure the body fat of the user based on the corrected impedance.

The apparatus may further include smart glasses in which the camera device is implemented, wherein the processor, the sensor, and the controller may be implemented in a smart watch, and the smart glasses may wirelessly communicate with the smart watch.

The camera device may photograph the image while the user is in contact with a hand of the user.

The camera device may photograph the image based on an input signal from the user.

According to an aspect of another exemplary embodiment, there is provided a wearable device of measuring a body fat including: a sensor or configured to measure an impedance of a user in response the sensor being in contact with a wrist of the user; a processor configured to measure, from an image including the wrist and the wearable device, a wrist tilt angle that the wrist is tilted sideways; and a controller configured to determine a variation rate of the impedance based on the wrist tilt angle.

The sensor may be further configured to detect a contact area that the wearable device and the wrist are in contact with each other and generate information indicating quality of contact based on the detected contact area, and the controller may be further configured to adjust the determined variation rate based on the information generated by the sensor.

BRIEF DESCRIPTION OF THE DRAWINGS

The above and/or other aspects will be more apparent and readily appreciated from the following description of certain exemplary embodiments with reference to the accompanying drawings in which:

FIGS. 3A and 3B illustrate a method of correcting an impedance measured by a sensor included in a wearable device, according to another exemplary embodiment;

FIG. 4 illustrates an example a method of correcting an impedance measured by a sensor included in a wearable device, according to another exemplary embodiment;

FIG. 5 is a flowchart of a method of correcting an impedance measured by a sensor included in the wearable device, according to another exemplary embodiment;

DETAILED DESCRIPTION

Figure 1:
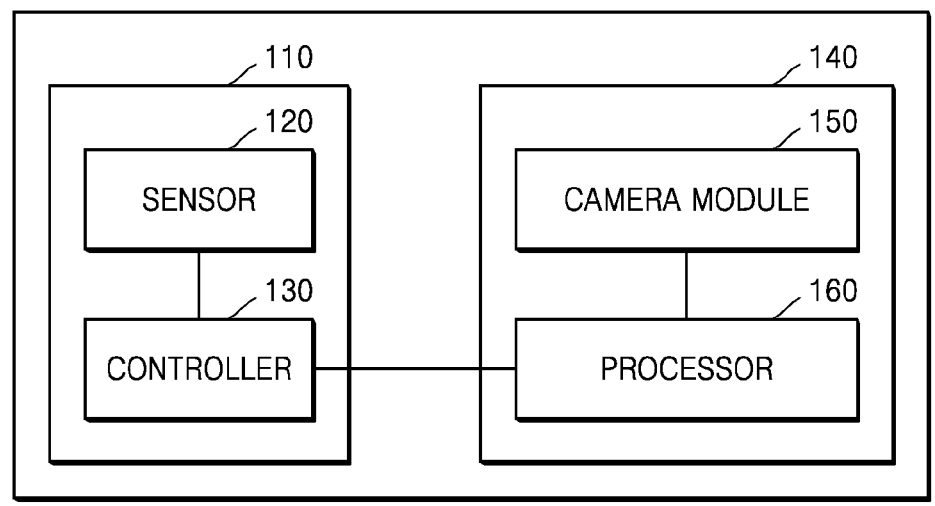
FIG. 1 is a block diagram of an apparatus for correcting an impedance measured by a sensor included in a wearable device, according to an exemplary embodiment.

Reference will now be made to the exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Exemplary embodiments are provided so that this disclosure will be thorough and complete, and will fully convey the concept of the inventive concept to those skilled in the art, and the scope of the exemplary embodiments of the inventive concept are defined by the appended claims. As used herein, the term "and/or" includes any and all combinations of one or more of the associated listed items. Expressions such as "at least one of," when preceding a list of elements, should be understood to modify the entire list of elements and not to modify the individual elements of a list.

Terms used herein will be briefly described, and are described below.

General and widely-used terms have been employed herein, in consideration of functions that are provided in various exemplary embodiments, and may vary according to an intention of one of ordinary skill in the art, a precedent, or emergence of new technologies. Additionally, in some cases, an user may arbitrarily select specific terms. Then, the applicant will provide the meaning of the terms in the description of the inventive concept. Accordingly, It will be understood that the terms, used herein, should be interpreted as having a meaning that is consistent with their meaning in the context of the relevant art and are not to be interpreted in an idealized or overly formal sense unless expressly defined herein.

It will be further understood that the terms "comprises," "comprising," "includes," and/or "including," when used herein, specify the presence of components, but do not preclude the presence or addition of one or more other components, unless otherwise specified. Additionally, a term 'unit' may refer to software or hardware components such as field programmable gate array (FPGA) or application-specific integrated circuit (ASIC). However, a "unit" is not limited to hardware or software. A "unit" may be included in a storage medium that may be addressed, or be one or more processors. Accordingly, as an example, a "unit" includes components such as software components, object-oriented software components, class components, task components, processes, functions, attributes, procedures, subroutines, segments of a program code, drivers, firmware, micro-codes, circuits, data, database, data structures, tables, arrays, variables, and the like. Functions provided in components or "units" may be combined into a smaller number of components or "units", or separated into additional components or "units".

Examples herein are further described with reference to the accompanying drawings, in which exemplary embodiments of the inventive concept are shown. In the description of exemplary embodiments, certain detailed explanations of the related art may be omitted if such a description may unnecessarily obscure the essence of one or more of the exemplary embodiments.

FIG. 1 is a block diagram of an apparatus 100 for correcting an impedance measured by a sensor 120 included in a wearable device 110, according to an exemplary embodiment. As shown in FIG. 1, the apparatus 100 includes a wearable device 110 and a photographing apparatus 140. The wearable device 110 may include a sensor 120 and a controller 130. The photographing apparatus 140 may include a camera module 150 and an processor 160. In this example, the wearable device 110 may be a smart watch and the photographing apparatus 140 may be smart glasses that are equipped with the camera module 150. Although FIG. 1 describes that the processor 150 is implemented in the photographing apparatus 140, embodiments are not limited thereto. The processor 150 may be implemented in the wearable device 110 so that the wearable device 110 includes the sensor 120, the controller 130, and the processor 160.

The camera module 150 may photograph an image that includes the wearable device 110 and both arms of a user. Accordingly, the camera module 150 may photograph a moving picture that includes the wearable device 110 and both arms of the user while a hand of the user contacts the wearable device 110 and both arms of the user are moving.

While the hand of the user contacts the wearable device 110, the camera module 150 may photograph an image that includes the wearable device 110 and both elbow joints of the user. For example, if the user wears the wearable device 110 on the left wrist, the user may contact the wearable device 110 with the right hand. As another example, while the user contacts the wearable device 110 with the right hand, the camera module 150 may photograph an image that includes the wearable device 110 and both arms of the user.

Additionally, the camera module 150 may photograph an image that includes the wearable device 110 and both arms of the user based on an input signal by the user. For example, if the user inputs a signal to the wearable device 110 to measure a body fat of the user, the wearable device 110 may transmit an input signal to the photographing apparatus 140. When the photographing apparatus 140 receives the input signal, the camera module 150 included in the photographing apparatus 140 may photograph an image that includes the wearable device 110 and both arms of the user.

For example, the processor 160 may measure an angle between straight lines respectively connecting the photographing apparatus 140 and both elbow joints, an angle between a straight line connecting the left elbow joint and the wearable device 110 and a straight line connecting the left elbow joint and the photographing apparatus 140, an angle between a straight line connecting a right elbow joint and the wearable device 110 and a straight line connecting the right elbow joint and the photographing apparatus 140, and an angle between straight lines respectively connecting the elbow joints and the wearable device 110. As another example, the processor 160 may measure an angle in consideration of a location of the camera module 150. The processor 160 is described with reference to FIG. 2.

Figure 2:
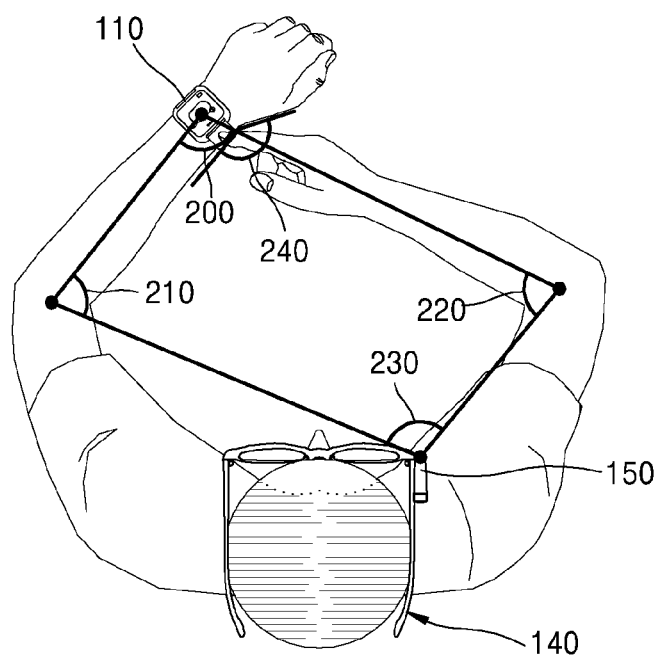
FIG. 2 illustrates a method of correcting an impedance measured by a sensor that is included in the wearable device, according to an exemplary embodiment.

FIG. 2 illustrates an example of a method of correcting an impedance measured by a sensor included in the wearable device 110, according to an exemplary embodiment. As shown in FIG. 2, the processor 160 may measure an angle 200 between straight lines that respectively connect the wearable device 110 and both elbow joints of a user, using an image photographed by the camera module 150. The processor 160 may measure an angle 210 that is between a straight line connecting the left elbow joint and the wearable device 110 and a straight line connecting the left elbow joint and the camera module 150, using an image photographed by the camera module 150.

For example, the processor 160 may measure an angle 220 between a straight line connecting a right elbow joint and the wearable device 110 and a straight line connecting the right elbow joint and the photographing apparatus, using an image photographed by the camera module 150. The processor 160 may measure an angle 230 between straight lines respectively connecting the camera module 150 and both elbow joints, using an image photographed by the camera module 150. The processor 160 may also measure a tilt angle 240 of the wrist which the wearable device 110 is put on. The tilt angle 240 may refer to an angle of the wrist which is tilted sideways. The sensor 120 shown in FIG. 1 is used in this example.

The sensor 120 may measure an impedance with respect to a wrist of a user. Additionally, the sensor 120 may repeatedly measure an impedance at a predetermined period of time. For example, the sensor may repeatedly measure an impedance of a user at a time period of 0.1 seconds. Additionally, the wearable device 110 may be equipped with one or more sensors 120. For example, the wearable device 110 may measure an impedance of a user by using four sensors 120.

As shown in one or more exemplary embodiments, the wearable device 110 and the camera module 140 may communicate with each other, for example, between the controller 130 and the processor 160. As another example, the wearable device 110 and the camera module 140 may each include at least one of a transmitter, a receiver, a transceiver, and the like, which may be used to perform communication.

The controller 130 may determine an impedance variation rate by using one or more of the measured angles. Additionally, the controller 130 may determine a variation rate of the impedance using variation rates of a predetermined impedance which correspond to the measured angles. An example of the predetermined impedance is described with reference to FIGS. 3A, 3B, and 4.

FIGS. 3A and 3B illustrate an example of a method of correcting an impedance measured by a sensor included in the wearable device 110, according to other exemplary embodiments. As shown in FIG. 3A, the camera module 150 may photograph a moving picture that includes the wearable device 110 and both arms of the user while a hand of the user contacts the wearable device 110. The processor 160 may measure an angle between straight lines that respectively connecting the camera module 150 and both elbow joints, an angle between a straight line connecting the left elbow joint and the wearable device 110 and a straight line connecting the left elbow joint and the camera module 150, an angle between a straight line connecting the right elbow joint and the wearable device 110 and a straight line connecting the right elbow joint and the camera module 150, and an angle between straight lines respectively connecting the elbow joints and the wearable device 110, by using the moving pictures photographed by the camera module 150.

For example, in FIG. 3A, the processor 160 may measure an angle 300 between straight lines respectively connecting the elbow joints and the wearable device 110, using pictures photographed by the camera module 150. The processor 160 may measure an angle 310 between a straight line connecting the left elbow joint and the wearable device 110 and a straight line connecting the left elbow joint and the camera module 150, by using the moving pictures photographed by the camera module 150. The processor 160 may measure an angle 320 between a straight line connecting the right elbow joint and the wearable device 110 and a straight line connecting the right elbow joint and the camera module 150, by using an image photographed by the camera module 150. The processor 160 may measure an angle 330 between straight lines respectively connecting the photographing apparatus and both elbow joints, by using the image photographed by the camera module 150.

FIG. 3B illustrates a diagram of a situation in which the user moves both arms so that his/her hands approach the chest. In FIG. 3B, the processor 160 may measure an angle 340 between straight lines respectively connecting the elbow joints and the wearable device 110, by using moving pictures photographed by the camera module 150. The processor 160 may measure an angle 350 between a straight line connecting the left elbow joint and the wearable device 110 and a straight line connecting the left elbow joint and the camera module 150, by using the moving pictures photographed by the camera module 150. The processor 160 may measure an angle 360 between a straight line connecting the right elbow joint and the wearable device 110 and a straight line connecting the right elbow joint and the camera module 150, by using an image photographed by the camera module 150. The processor 160 may measure an angle 370 between straight lines respectively connecting the photographing apparatus and both elbow joints, by using an image photographed by the camera module 150.

For example, the sensor 120 may consecutively measure an impedance of a user when the sensor 120 is in contact with a wrist of the user while the user moves from a position shown in FIG. 3A to the position shown in FIG. 3B. In response, the controller 130 may set impedance variation rates that correspond to respective measured angles by using the measured impedance that respectively correspond to the measured angles. An example of the impedance variation rate is described with reference to FIG. 4.

FIG. 4 illustrates an example of a table including an impedance variation rate 410 according to the angle 200 between straight lines respectively connecting the elbow joints and the wearable device 110, the angle 210 between a straight line connecting the left elbow joint and the wearable device 110 and a straight line connecting the left elbow joint and the camera module 150, the angle 220 between a straight line connecting the right elbow joint and the wearable device 110 and a straight line connecting the right elbow joint and the camera module 150, and the angle 230 between straight lines respectively connecting the camera module and both elbow joints. As a non-limiting example, if the angle 200 between straight lines respectively connecting the elbow joints and the wearable device 110 is 100°, the angle 210 between a straight line connecting the left elbow joint and the wearable device 110 and a straight line connecting the left elbow joint and the camera module 150 is 80°, the angle 220 between a straight line connecting the right elbow joint and the wearable device 110 and a straight line connecting the right elbow joint and the camera module 150 is 60°, and the angle 230 between straight lines respectively connecting the camera module 150 and both elbow joints is 60°, the controller 130 may determine the impedance variation rate 410 as being equal to a variable of 0.8.

As another example, if the angle 200 between straight lines respectively connecting the elbow joints and the wearable device 110 is 80°, the angle 210 between a straight line connecting the left elbow joint and the wearable device 110 and a straight line connecting the left elbow joint and the camera module 150 is 100°, the angle 220 between a straight line connecting the right elbow joint and the wearable device 110 and a straight line connecting the right elbow joint and the camera module 150 is 80°, and the angle 230 between straight lines respectively connecting the camera module 150 and both elbow joints is 100°, the controller 130 may determine the impedance variation rate 410 as being equal to 0.6.

As another example, if the angle 200 between straight lines respectively connecting the elbow joints and the wearable device 110 is 60°, the angle 210 between a straight line connecting the left elbow joint and the wearable device 110 and a straight line connecting the left elbow joint and the camera module 150 is 120°, the angle 220 between a straight line connecting the right elbow joint and the wearable device 110 and a straight line connecting the right elbow joint and the camera module 150 is 100°, and the angle 230 between straight lines respectively connecting the camera module 150 and both elbow joints is 80°, the controller 130 may determine the impedance variation rate 410 as being equal to 0.4. If the angle 210 between a straight line connecting the left elbow joint and the wearable device 110 and a straight line connecting the left elbow joint and the camera module 150 and the angle 220 between a straight line connecting the right elbow joint and the wearable device 110 and a straight line connecting the right elbow joint and the camera module 150 are great, the user stretches the arm in approximately a straight line, and thus, an impedance variation rate is small. This is created because a measured impedance increases when a user bends his arms.

The table of FIG. 4 describes that the impedance variation rate 410 is determined by a combination of the four angles 200, 210, 220, and 230. However, embodiments are not limited thereto, and the impedance variation rates 410 may be determined based only on the angle 200 between straight lines respectively connecting the elbow joints and the wearable device 110. Also, the table may further include information indicating a impedance variation rate that corresponds to the tilt angle 240 of the wrist.

The controller 130 may correct an impedance using the determined impedance variation rate. For example, if an impedance measured by the sensor 120 is 10Ω (ohm) and the determined impedance variation is 0.4, the controller 130 may correct the impedance to be equal to 4Ω by multiplying the impedance by the impedance variation rate. In this example, the controller 130 may determine a variation rate of the impedance by using a predetermined relation between a measured angle and a variation rate of the impedance. For example, the controller 130 may perform a function for obtaining or generating a variation rate using a relation between the four angles 200 through 230. In other words, the controller 130 may determine a variation rate of the impedance by inputting the four angles 200 through 230 as four variables of a function f(a,b,c,d). The controller 130 may measure body fat of the user by using the corrected impedance. According to an exemplary embodiment, the controller 130 may adjust the corrected impedance based on quality of a contact between the wearable device 110 and the user. The sensor 120 may provide information indicating the quality of the contact by detecting an actual contact area where the wearable device 110 is actually contacted with the user. The controller 130 may determine the quality of the contact based on a maximum contact area of the wearable device 110 and the actual contact area.

FIG. 5 is a flowchart illustrating a method of correcting an impedance measured by a sensor included in a wearable device, according to an exemplary embodiment. As shown in FIG. 5, the method of correcting an impedance measured by the sensor 120 included in the wearable device 110 includes operations that are processed in a time series by the apparatus 100 for correcting an impedance which is shown in FIG. 1. Accordingly, it should be understood that descriptions provided with regard to the apparatus 100 shown in FIG. 1 may also apply to the method described in the example with reference to FIG. 5, even though the descriptions are not provided here again.

In operation S500, an image that includes the wearable device and both arms of a user is photographed.

In operation S510, an angle between straight lines respectively connecting a camera module and both elbow joints, an angle between a straight line connecting the left elbow joint and the wearable device and a straight line connecting the left elbow joint and the camera module, an angle between a straight line connecting the right elbow joint and the wearable device and a straight line connecting the right elbow joint and the camera module, and an angle between straight lines respectively connecting the elbow joints and the wearable device are measured using the photographed image.

In operation S520, an impedance of the user is measured when a wrist of the user is in contact with the sensor included in the wearable device.

In operation S530, an impedance variation rate is determined by using the measured angle.

In operation S540, the impedance is corrected using the determined impedance variation rate.

Figure 6:
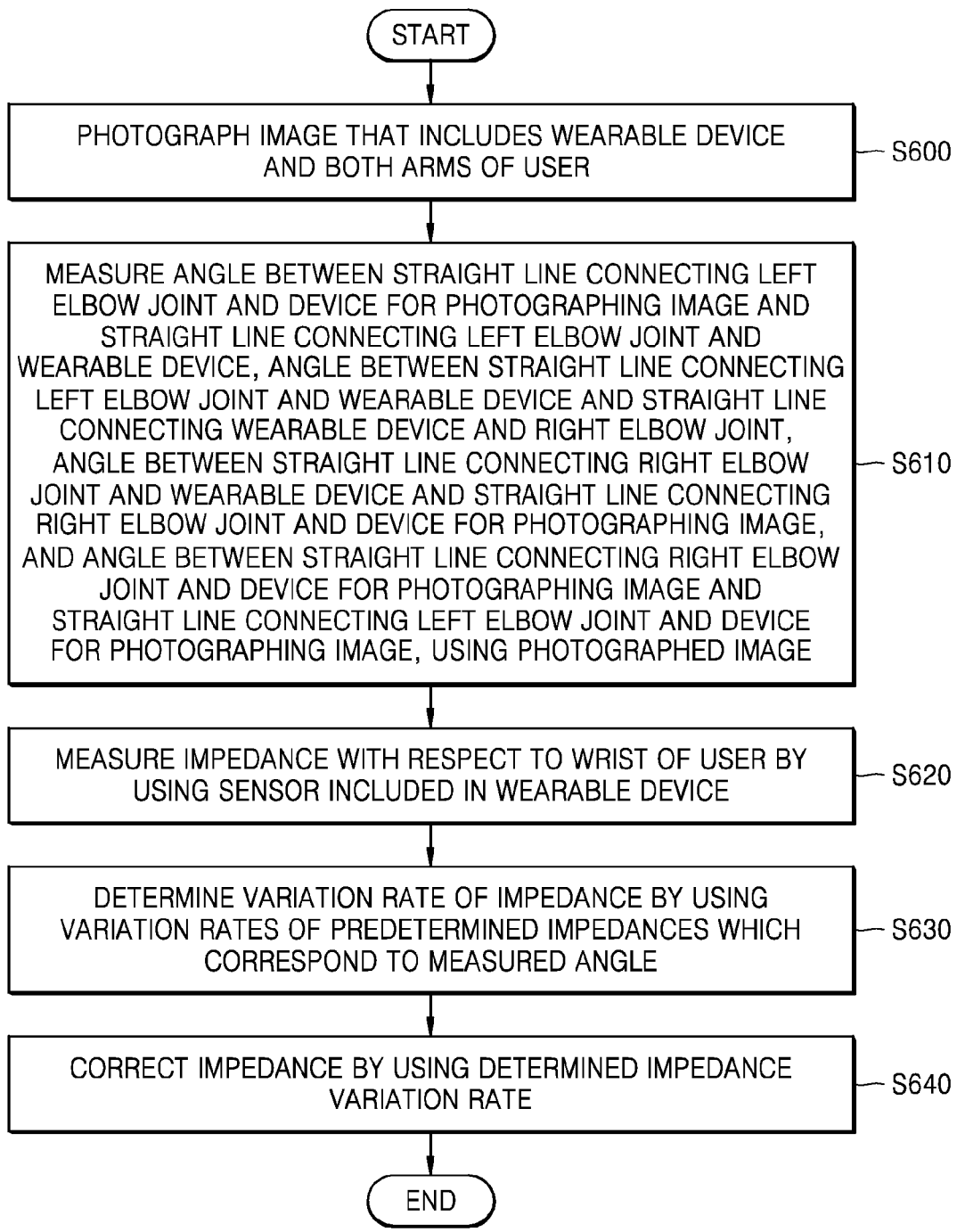
FIG. 6 is a flowchart of a method of correcting an impedance measured by a sensor included in the wearable device, according to another exemplary embodiment.

FIG. 6 is a flowchart of a method for correcting an impedance measured by a sensor included in a wearable device, according to an exemplary embodiment. As shown in FIG. 6, the method of correcting an impedance, for example, measured by the sensor 120 included in the wearable device 110 includes operations that are processed in a time series by the apparatus 100 for correcting an impedance as shown in FIG. 1. Accordingly, it should be understood that the exemplary embodiments that are provided with regard to the apparatus 100 shown in FIG. 1, may also apply to the example of the method described with reference to FIG. 6, even though the descriptions are not provided here again.

In operation S600, an image that includes the wearable device and both arms of a user is photographed.

In operation S610, an angle between straight lines respectively connecting a camera module and both elbow joints, an angle between a straight line connecting the left elbow joint and the wearable device and a straight line connecting the left elbow joint and the camera module, an angle between a straight line connecting the right elbow joint and the wearable device and a straight line connecting the right elbow joint and the camera module, and an angle between straight lines respectively connecting the elbow joints and the wearable device is measured using the photographed image.

In operation S620, an impedance of the user is measured when a wrist of the user is in contact with the sensor included in the wearable device.

In operation S630, a variation rate of the impedance is determined using a variation rate of the predetermined impedance which corresponds to the measured angle.

In operation S640, the impedance may be corrected by using the determined variation rate of the impedance.

Figure 7:
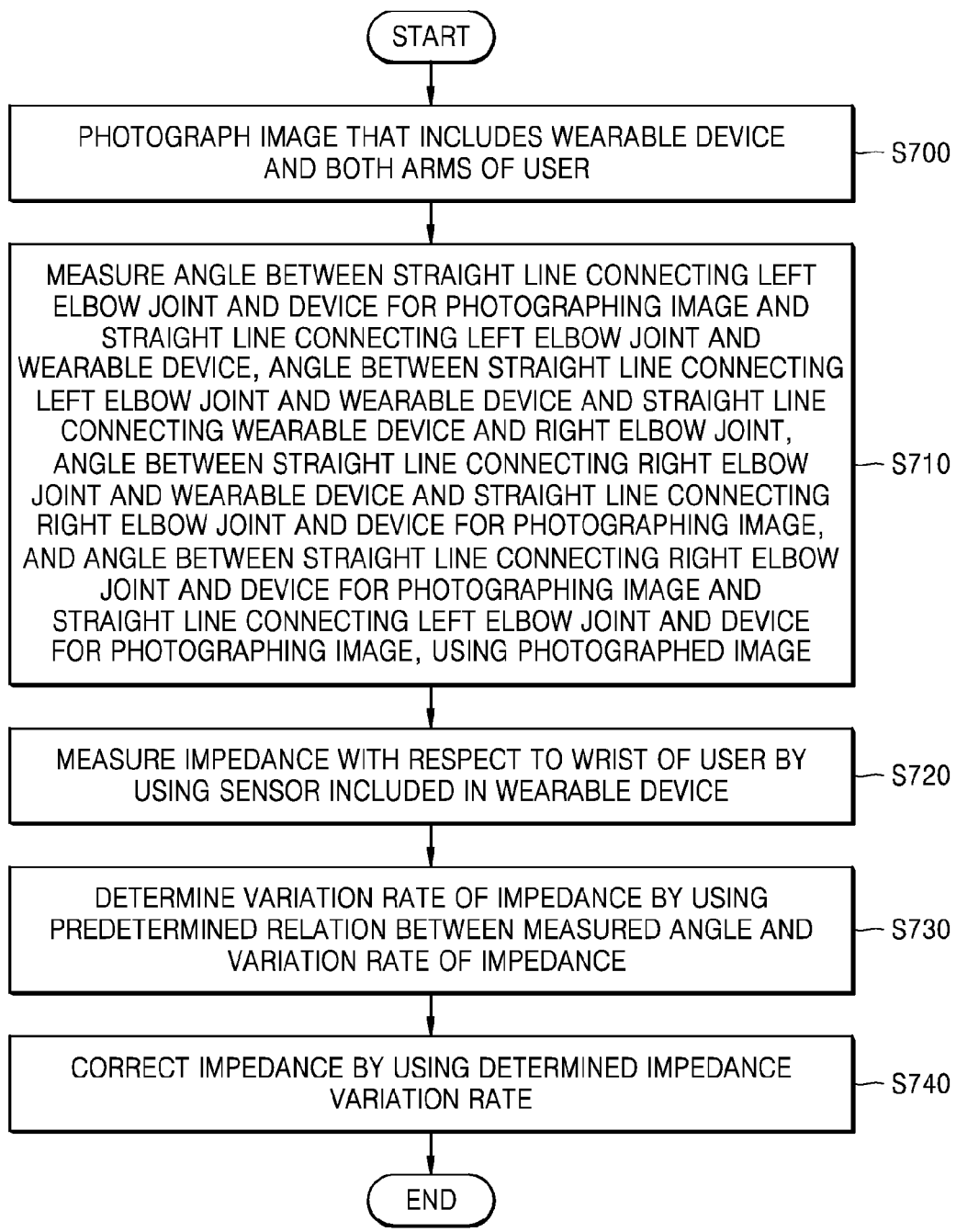
FIG. 7 is a flowchart of a method of correcting an impedance measured by a sensor included in the wearable device, according to another exemplary embodiment.

FIG. 7 is a flowchart of a method of correcting an impedance measured by a sensor included in a wearable device, according to another embodiment.

As shown in FIG. 7, the method of correcting an impedance measured by the sensor 120 included in the wearable device 110 includes operations that are processed in a time series by the apparatus 100 for correcting an impedance which is shown in FIG. 1. Accordingly, it should be understood that descriptions provided with regard to the apparatus 100 shown in FIG. 1 may be apply to the method described with reference to FIG. 7, even though the description are not provided here again.

In operation S700, an image that includes the wearable device and both arms of a user may be photographed.

In operation S710, an angle between straight lines respectively connecting a camera module and both elbow joints, an angle between a straight line connecting the left elbow joint and the wearable device and a straight line connecting the left elbow joint and the camera module, an angle between a straight line connecting the right elbow joint and the wearable device and a straight line connecting the right elbow joint and the camera module, and an angle between straight lines respectively connecting the elbow joints and the wearable device are measured using the photographed image.

In operation S720, an impedance the user is measured when a wrist of the user is in contact with the sensor included in the wearable device.

In operation S730, a variation rate of the impedance is determined by using a predetermined relation between the measured angle and the variation rate of the impedance.

In operation S740, the impedance is corrected by using the determined variation rate of the impedance.

In addition, other embodiments of the inventive concept can also be implemented through computer-readable code/instructions in/on a medium, e.g., a computer-readable medium, to control at least one processing element to implement any above described embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more embodiments of the inventive concept. The media may also be a distributed network, so that the computer-readable code is stored/transferred and executed in a distributed fashion.

Furthermore, the processing element could include a processor or a computer processor, and processing elements may be distributed and/or included in a single device.

Embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more microprocessors or other control devices. Similarly, where the elements of the inventive concept are implemented using software programming or software elements the inventive concept may be implemented with any programming or scripting language such as C, C++, Java, assembler, or the like, with the various algorithms being implemented with any combination of data structures, objects, processes, routines or other programming elements. Functional aspects may be implemented via algorithms executed by one or more processors. Furthermore, embodiments could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The embodiments shown and described herein are illustrative examples of the inventive concept and are not intended to otherwise limit the scope of the embodiments in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents for describing the inventive concept (especially in the context of the following claims) is to be construed to cover both the singular and the plural. Furthermore, recitation of ranges of values herein is merely intended to function as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better present the inventive concept and does limit the scope of embodiments unless otherwise claimed. Additionally, it will be understood by those of ordinary skill in the art that various modifications, combinations, and changes can be formed according to design conditions and factors within the scope of the attached claims or the equivalents.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present inventive concept have been described with reference to the figures, it will be understood by those of ordinary skill in the art that various changes in form and details may be made therein without departing from the spirit and scope of the present inventive concept as defined by the following claims.

What is claimed is:

1. A method of correcting an impedance measured by a sensor comprised in a wearable device, the method comprising:
    measuring, from an image including the wearable device and arms of a user, by the wearable device, a first angle between a straight line connecting a left elbow joint of the user and a camera device for photographing the image and a straight line connecting the left elbow joint and the wearable device, a second angle between a straight line connecting the left elbow joint and the wearable device and a straight line connecting the wearable device and a right elbow joint of the user, a third angle between a straight line connecting the right elbow joint and the wearable device and a straight line connecting the right elbow joint and the camera device, and a fourth angle between a straight line connecting the right elbow joint and the camera device and a straight line connecting the left elbow joint and the camera device;
    measuring, by the sensor, the impedance of the user in response to the sensor being in contact with the user;
    determining, by the wearable device, a variation rate of the impedance based one at least one of the first, second, third, and fourth angles; and
    correcting, by the wearable device, the impedance based on the determined variation rate of the impedance.

2. The method of claim 1, wherein the determining comprises determining the variation rate of the impedance based on a predetermined variation rate of the impedance which corresponds to the first, second, third, and fourth angles.

3. The method of claim 2, wherein the determining further comprises:
    photographing a moving picture including the wearable device and the arms of the user while one hand of the user is in contact with the wearable device and the arms are moving;
    consecutively measuring impedance of the user by using the sensor while photographing the moving picture;
    measuring a fifth angle between a straight line connecting the left elbow joint of the user and the camera device and a straight line connecting the left elbow joint and the wearable device, a sixth angle between a straight line connecting the left elbow joint and the wearable device and a straight line connecting the wearable device and the right elbow joint of the user, a seventh angle between a straight line connecting the right elbow joint and the wearable device and a straight line connecting the right elbow joint and the camera device, and an eighth angle between a straight line connecting the right elbow joint and the camera device and a straight line connecting the left elbow joint and the camera device based on the moving picture; and
    setting a variation rate of the impedance in correspondence with the fifth, sixth, seventh, and eighth angles by using the impedance which corresponds to the first, second, third, and fourth angles.

4. The method of claim 3, wherein the consecutively measuring the impedance comprises repeatedly measuring the impedance at a predetermined time period.

5. The method of claim 1, wherein the determining comprises determining the variation rate of the impedance based on a predetermined relation between at least one of the first, second, third, and fourth angles and the variation rate of the impedance.

6. The method of claim 1, wherein the correcting comprises measuring a body fat of the user based on the corrected impedance.

7. The method of claim 1, wherein, the wearable device is a smart watch and the image is photographed by the camera device equipped with smart glasses.

8. The method of claim 7, further comprising photographing the image while the smart watch is in contact with one hand of the user.

9. The method of claim 1, further comprising photographing the image based on an input signal from the user.

10. An apparatus comprising:
    a processor configured to measure, from an image including an wearable device and arms of a user, a first angle between a straight line connecting a left elbow joint of the user and a camera device for photographing the image and a straight line connecting the left elbow joint and the wearable device, a second angle between a straight line connecting the left elbow joint and the wearable device and a straight line connecting the wearable device and a right elbow joint of the user, a third angle between a straight line connecting the right elbow joint and the wearable device and a straight line connecting the right elbow joint and the camera device, and a fourth angle between a straight line connecting the right elbow joint and the camera device and a straight line connecting the left elbow joint and the camera device;
    a sensor configured to measure an impedance of the user in response the sensor being in contact with the user; and
    a controller configured to determine a variation rate of the impedance based on at least one of the first, second, third, and fourth angles, and correct the impedance based on the determined variation rate of the impedance.

11. The apparatus of claim 10, further comprising the camera device configured to photograph the image including the wearable device and the arms of the user.

12. The apparatus of claim 10, wherein the controller is further configured to determine the variation rate of the impedance based on a predetermined variation rate of the impedance which corresponds to the first, second, third, and fourth angles.

13. The apparatus of claim 12, wherein the camera device is further configured to photograph a moving picture including the wearable device and the arms of the user while one hand of the user is in contact with the wearable device and the arms of the user are moving, the sensor is further configured to consecutively measure impedance of the user while the moving picture is being photographed, the processor is further configured to measure a fifth angle between a straight line connecting a left elbow joint of the user and the camera device and a straight line connecting the left elbow joint and the wearable device, a sixth angle between a straight line connecting the left elbow joint and the wearable device and a straight line connecting the wearable device and a right elbow joint of the user, a seventh angle between a straight line connecting the right elbow joint and the wearable device and a straight line connecting the right elbow joint and the camera device, and an eighth angle between a straight line connecting the right elbow joint and the camera device and a straight line connecting the left elbow joint and the camera device based on the moving picture, and the controller is further configured to set a variation rate of the impedance in correspondence with the fifth, sixth, seventh, and eighth angles by using the impedance corresponding to the first, second, third, and fourth angles.

14. The apparatus of claim 13, wherein the sensor is further configured to consecutively measure the impedance at a predetermined time period.

15. The apparatus of claim 10, wherein the controller is further configured to determine the variation rate of the impedance based on a predetermined relation between at least one of the first, second, third, and fourth angles and the variation rate of the impedances.

16. The apparatus of claim 10, wherein the controller is further configured to determine the body fat of the user based on the corrected impedance.

17. The apparatus of claim 10, further comprising smart glasses in which the camera device is implemented,
    wherein the processor, the sensor, and the controller are implemented in a smart watch, and
    wherein the smart glasses wirelessly communicate with the smart watch.

18. The apparatus of claim 17, wherein the camera device is further configured to photograph the image while the smart watch is in contact with a hand of the user.

19. The apparatus of claim 17, wherein the camera device is further configured photograph the image based on an input signal from the user.

20. A non-transitory computer readable storage medium storing a program that is executable by a computer to perform the method of claim 1.

* * * * *